United States Patent
Komulainen et al.

(10) Patent No.: US 10,449,415 B2
(45) Date of Patent: Oct. 22, 2019

(54) WRIST-WORN PHYSICAL ACTIVITY MEASUREMENT APPARATUS

(71) Applicant: Polar Electro Oy, Kempele (FI)

(72) Inventors: Olli Komulainen, Oulu (FI); Lauri Lumme, Oulu (FI)

(73) Assignee: Polar Electro Oy, Kempele (FI)

( * ) Notice: Subject to any disclaimer, the term of this patent is extended or adjusted under 35 U.S.C. 154(b) by 652 days.

(21) Appl. No.: 14/556,869

(22) Filed: Dec. 1, 2014

(65) Prior Publication Data

US 2016/0151669 A1    Jun. 2, 2016

(51) Int. Cl.
| | |
|---|---|
| A63B 24/00 | (2006.01) |
| G01C 22/00 | (2006.01) |
| A61B 5/11 | (2006.01) |
| A61B 5/00 | (2006.01) |
| A44C 5/10 | (2006.01) |
| A44C 5/00 | (2006.01) |

(52) U.S. Cl.
CPC .......... *A63B 24/0062* (2013.01); *A44C 5/105* (2013.01); *A61B 5/1118* (2013.01); *A61B 5/681* (2013.01); *G01C 22/006* (2013.01); *A44C 5/0015* (2013.01)

(58) Field of Classification Search
CPC ............................ A44C 5/105; A63B 24/0062
USPC ................. 702/160; 368/281; 59/80; 24/365
See application file for complete search history.

(56) References Cited

U.S. PATENT DOCUMENTS

| | | | | |
|---|---|---|---|---|
| 2010/0331145 A1* | 12/2010 | Lakovic | .................. | G04F 10/00 482/8 |
| 2011/0166461 A1* | 7/2011 | Susstrunk | .............. | A61B 5/021 600/494 |
| 2011/0288382 A1 | 11/2011 | Finburgh et al. | | |
| 2013/0106603 A1* | 5/2013 | Weast | ..................... | G06F 1/163 340/539.11 |
| 2015/0145673 A1* | 5/2015 | Choi | .................... | A61B 5/6843 340/539.12 |
| 2015/0289087 A1* | 10/2015 | Oki | ........................ | H04W 4/02 705/6 |
| 2015/0335284 A1* | 11/2015 | Nuovo | ................. | A61B 5/0022 600/301 |

FOREIGN PATENT DOCUMENTS

| | | |
|---|---|---|
| CH | 482421 | 12/1969 |
| EP | 0557578 A1 | 9/1993 |

OTHER PUBLICATIONS

European Search Report for corresponding European Patent Application No. 15196228, pp. 1-2 (dated Apr. 20, 2016).

* cited by examiner

*Primary Examiner* — Hoai V Ho
*Assistant Examiner* — Muna A Techane
(74) *Attorney, Agent, or Firm* — FisherBroyles, LLP

(57) ABSTRACT

A wrist-worn physical activity measurement apparatus is disclosed. The apparatus includes a bracelet comprising a plurality of links, each link being formed at one side to comprise a part and at the opposite side a counterpart interlocking with a part of an adjacent link, and a flexible casing encasing the plurality of the links. The apparatus is attachable around a curvature of a wrist of a user such that the links and the adjacent links are pivotably lockable in relation to each other in order to wrap and lock around the wrist.

17 Claims, 4 Drawing Sheets

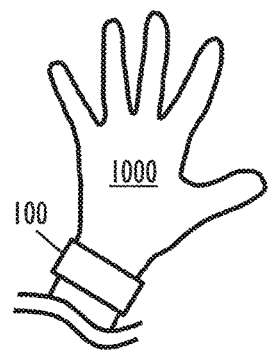
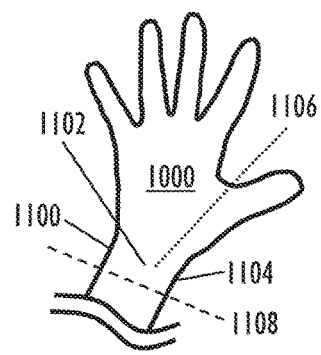
FIG. 10     FIG. 11
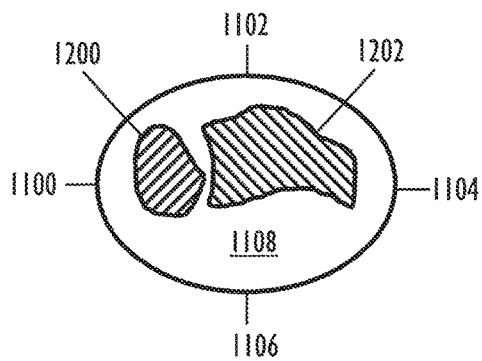
FIG. 12
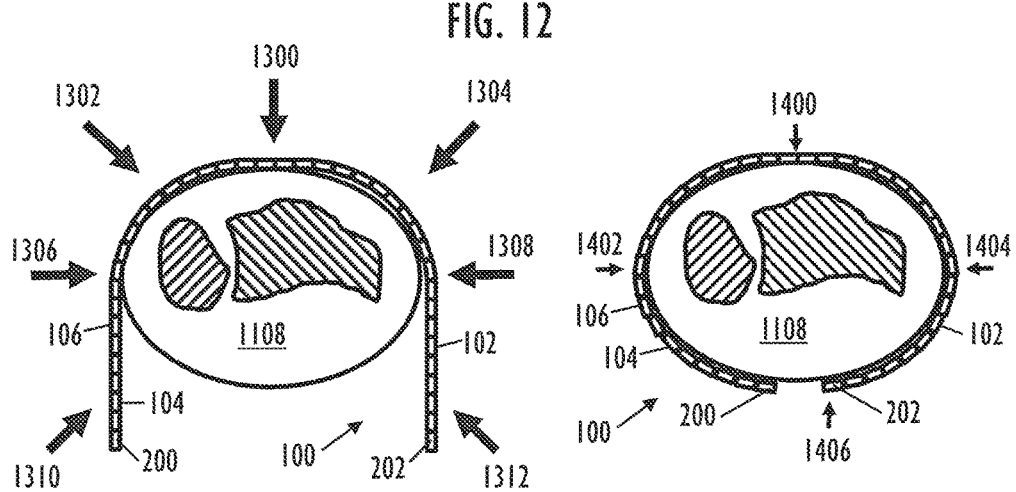
FIG. 13     FIG. 14

WRIST-WORN PHYSICAL ACTIVITY MEASUREMENT APPARATUS

BACKGROUND

Field

The invention relates to a wrist-worn physical activity measurement apparatus.

Description of the Related Art

Wrist-worn apparatuses capable of a physical activity measurement such as sports watches utilize a bracelet for attaching the apparatus around the wrist. Usability of the apparatus may be affected by how easy and comfortable it is to attach, wear and take off the apparatus.

SUMMARY

The present invention seeks to provide an improved wrist-worn physical activity measurement apparatus.

According to an aspect of the present invention, there is provided an apparatus as specified in claim 1.

BRIEF DESCRIPTION OF THE DRAWINGS

Example embodiments of the present invention are described below, by way of example only, with reference to the accompanying drawings, in which

FIGS. 10, 11, 12, 13 and 14 illustrate example embodiments of a use of the apparatus.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrates various example embodiments of the apparatus 100, they are only a simplified block diagrams that only shows some structures and functional entities. It is apparent to a person skilled in the art that the described apparatus 100 may also comprise other functions and structures. It should be appreciated that details of some functions and structures, are irrelevant to the actual invention. Therefore, they need not be discussed in more detail here.

Figure 1:
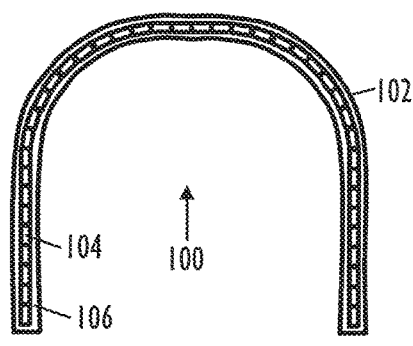
FIGS. 1, 2, 3, 4, 5, 6, 7, 8 and 9 illustrate example embodiments of a structure of an apparatus.

FIG. 1 illustrates an example embodiment of a structure of a wrist-worn physical activity (such as sports, exercise or other physical activity) measurement apparatus 100.

The apparatus 100 comprises a bracelet 102 comprising a plurality of links 104, and a flexible casing 106 encasing the plurality of the links 104.

Figure 2:
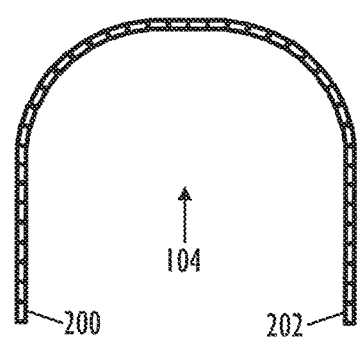

FIG. 2 illustrates the plurality of the links 104: in this example embodiment there are forty links forming a chain from the first link 200 to the last link 202, but, naturally, the number and size of the links 104 may vary in order to accommodate wrists with varying circumferences.

In an example embodiment, the apparatus 100 further comprises an electronics module coupled with the bracelet 102.

Figure 3:
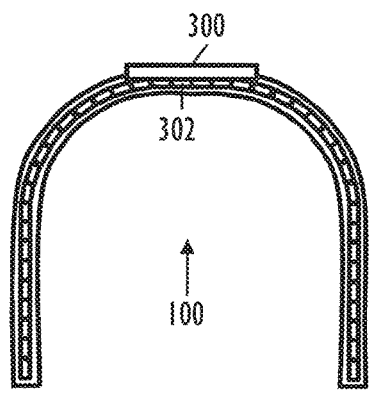

In an example embodiment of FIG. 3, the electronics module 300 is attached to at least one 302 of the links 104: in this example embodiment to six of the links 104, but, naturally, the number of the links 104 may vary as required in order to achieve the required fixing.

Figure 4:
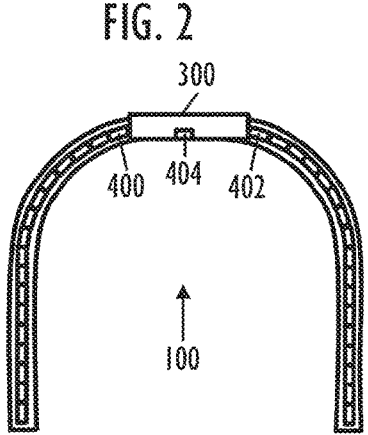

In an example embodiment of FIG. 4, the electronics module 300 is attached between two 400, 402 of the links 104.

Figure 5:
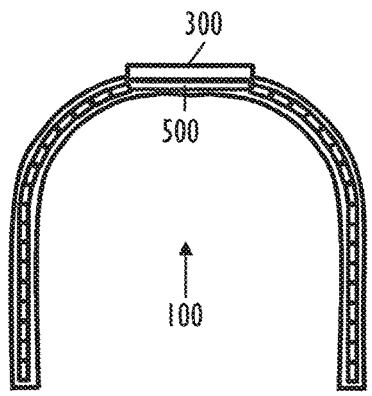

In an example embodiment of FIG. 5, at least one 500 of the links 104 is a special link, in which the electronics module 300 is integrated.

In an example embodiment, the electronics module 300 comprises a biosignal measurement sensor, and/or a processor module comprising one or more processors and one or more memories including computer program code.

FIG. 4 further illustrates an example embodiment, wherein the electronics module 300 comprises a biosignal measurement sensor 404. In an example embodiment, the measurement sensor 404 is an optical measurement sensor capable of measuring heart rate information from the wrist of the user. In an example embodiment, the optical measurement sensor 404 operates as follows: at least one LED projects light on the skin of the wrist, whereupon an electro-optical cell detects heart rate by examining pulsing volume of blood flow in the wrist.

Figure 6:
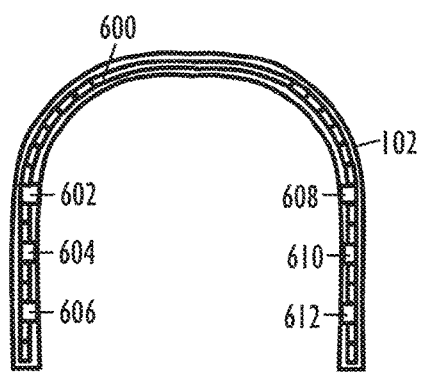

FIG. 6 illustrates an example embodiment, wherein the electronics module 300 is distributed in the bracelet 102: a main electronics module 600 communicates with a plurality of measurement sensors 602, 604, 606, 608, 610, 612. In an example embodiment, the measurement sensors 602, 604, 606, 608, 610, 612 are bioimpedance measurement sensors capable of measuring physiological parameters such as heart rate information from the wrist of the user. In an example embodiment, the bioimpedance measurement sensors 602, 604, 606, 608, 610, 612 measure the resistance of wrist tissue to an electric current in order to capture physiological signals of the user. In an example embodiment, the measurement sensors 602, 604, 606, 608, 610, 612 are coupled with the main electronics module 600 by conductors, which may run inside the bracelet 102 independently, or integrated with the links 104 or the flexible encasing 106.

Besides these two types of biosignal measurement sensors, also other types of biosignal measurement sensors may be embedded into the electronics module 300. These types include but are not limited to the following: a PPG (photoplethysmography) sensor, a Laser Doppler-based blood flow sensor, a magnetic blood flow sensor, an EMFI pulse sensor, a polarization blood flow sensor.

FIG. 6 also illustrates an example embodiment, wherein the main electronics module 600 is of flexible material which adapts to the curvature of the wrist. Accordingly, the electronics module 300 may be embedded inside a (possibly waterproof) casing, or, alternatively, the electronics module 600 may be implemented with flexible printed electronics.

Figure 7:
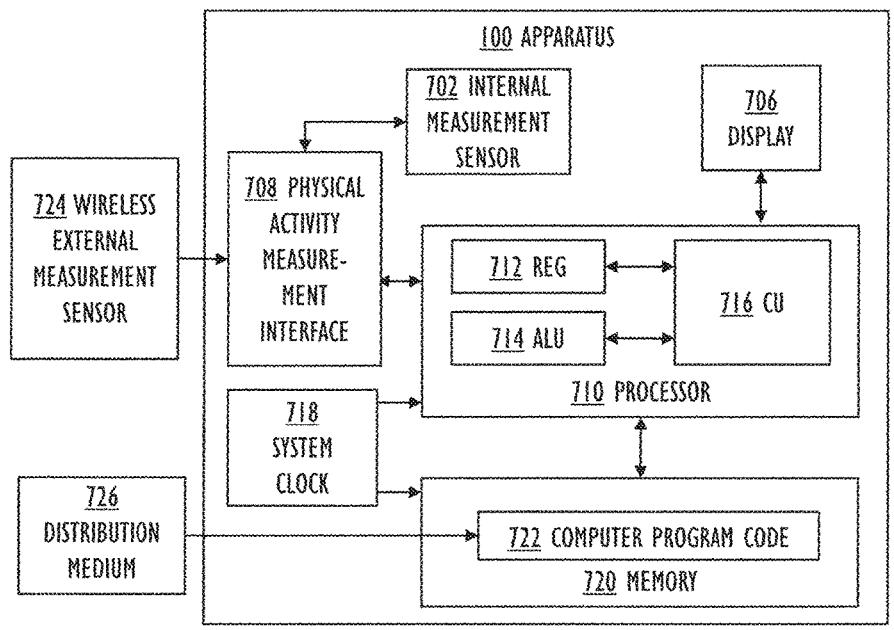

FIG. 7 illustrates an example embodiment, wherein the apparatus 100 comprises the electronics module 300, 600, which comprises one or more processors 710, and one or more memories 720 including computer program code 722. The one or more memories 720 and the computer program code 722 are configured to, with the one or more processors 710, cause the apparatus 100 at least to perform a function related to a physical activity measurement on the user, wherein the function comprises at least one of a control of an apparatus 100 internal sensor 702 measuring functioning of the body of the user, a control of an apparatus 100 external sensor 724 measuring functioning of the body of the user, a control of a heart rate measurement of the user, a control of an acceleration measurement related to a movement of the user, a control of a well-being measurement of the user.

In an example embodiment, the apparatus 100 comprises a physical activity measurement sensor interface 708, which may be utilized to obtain measurement data obtained by monitoring a user of the apparatus 100.

The sensors 702, 724 may produce the physical activity-related measurement data such as sports, exercise or activity related data. A non-exhaustive list of sensors 702, 724 includes heart rate sensors, motion sensors, location sensors, swimming sensors and bike sensors, as well as other sensors gathering information regarding the training. The heart rate sensors include, but are not limited to, a cardiovascular sensor (such as an electrocardiogram ECG sensor), an optical heart rate sensor (heart rate, heart rate variability), and a bioimpedance sensor. Motion sensors may include accelerometers worn on chest, wrist, or ankle, for example. Location sensors may utilize GPS (Global Positioning System) or other satellite-based, or radio system-based system for locating the user and measuring various parameters (speed, distance, location, route) relating to the movement of the user. Swimming sensors may measure swimming specific parameters such as number of strokes or distance, for example. Bike sensors may be sensors attached to various parts of the bike for measuring speed, cadence, or power, for example. The gathered sensor information may be utilized to calculate further physical activity-related measurement data of the user such as total energy consumption, an energy consumption speed, an activity level, a cumulated activity, for example.

As illustrated in FIG. 7, the sensors may be internal measurement sensors 702 (within the apparatus 100) and/or wireless external measurement sensors 724 (outside of the apparatus 100). The apparatus 100 may comprise a transceiver communicating with the wireless external measurement sensor(s) 724, or even just a receiver for receiving measurements from the wireless external measurement sensors 724. For the internal measurement sensors 702, the interface 708 may be a suitable hardware communication interface such as a wired interface or an appropriate communication bus.

The term 'processor' 710 refers to a device that is capable of processing data. Depending on the processing power needed, the apparatus 100 may comprise several processors 710 such as parallel processors or a multicore processor. When designing the implementation of the processor 710, a person skilled in the art will consider the requirements set for the size and power consumption of the apparatus 100, the necessary processing capacity, production costs, and production volumes, for example. The processor 710 and the memory 720 may be implemented by an electronic circuitry.

The term 'memory' 720 refers to a device that is capable of storing data run-time (=working memory) or permanently (=non-volatile memory). The working memory and the non-volatile memory may be implemented by a random-access memory (RAM), dynamic RAM (DRAM), static RAM (SRAM), a flash memory, a solid state disk (SSD), PROM (programmable read-only memory), a suitable semiconductor, or any other means of implementing an electrical computer memory.

In an example embodiment, a system clock 718 constantly generates a stream of electrical pulses, which cause the various transferring operations within the apparatus 100 to take place in an orderly manner and with specific timing.

In an example embodiment, the processor 710 may be implemented as a microprocessor implementing functions of a central processing unit (CPU) on an integrated circuit. The CPU is a logic machine executing a computer program code 722. The computer program code 722 may be coded as a computer program using a programming language, which may be a high-level programming language, such as C++, C, or Java, or a low-level programming language, such as a machine language, or an assembler. The CPU may comprise a set of registers 712, an arithmetic logic unit (ALU) 714, and a control unit (CU) 716. The control unit 716 is controlled by a sequence of the computer program code 722 transferred to the CPU from the (working) memory 720. The control unit 716 may contain a number of microinstructions for basic operations. The implementation of the microinstructions may vary, depending on the CPU design. The microprocessor 710 may also have an operating system (a dedicated operating system of an embedded system, a real-time operating system, or even a general-purpose operating system), which may provide the computer program code 722 with system services.

A non-exhaustive list of implementation techniques for the processor 710 and the memory 720 includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

The computer program code 722 may be implemented by software and/or hardware. In an example embodiment, the software may be written by a suitable programming language, and the resulting executable code 722 may be stored on the memory 720 and run by the processor 710.

In an example embodiment, the functionality of the hardware may be designed by a suitable hardware description language (such as Verilog or VHDL), and transformed into a gate-level netlist (describing standard cells and the electrical connections between them), and after further phases the chip implementing the processor 710, memory 720 and the code 722 of the apparatus 100 may be fabricated with photo masks describing the circuitry.

In an example embodiment, the processor 710 and the memory 720 of the apparatus 100 are a part of a microcontroller.

In an example embodiment, the processor 110 and the memory 120, and the other electronic circuits 404, 602, 604, 606, 608, 610, 612 are separate entities, communicatively coupled together by an appropriate serial bus, for example. In general, interfaces between the various elements may be implemented with suitable interface technologies, such as a message interface, a method interface, a sub-routine call interface, a block interface, an appropriate serial/parallel bus, or any hardware/software means enabling communication between various sub-units of the apparatus 100.

An example embodiment provides a computer-readable medium 726 for the apparatus 100 comprising a computer program comprising the computer program code 722. Said computer program code 722, when loaded into the apparatus 100 and executed in the apparatus 100, causes the apparatus 100 to perform the function(s) related to the physical activity measurement on the user. In an example embodiment, the computer program code 722 may be in source code form, object code form, executable file, or in some intermediate form. The computer-readable medium 726 may comprise at least the following: any entity or device capable of carrying computer program code 722 to the apparatus 100, a record medium, a computer memory, a read-only memory, an electrical carrier signal, a telecommunications signal, and a software distribution medium. In some jurisdictions, depending on the legislation and the patent practice, the computer-readable medium 726 may not be the telecommunications signal. In an example embodiment, the computer-readable medium 726 may be a non-transitory computer readable storage medium.

In an example embodiment, the apparatus 100 comprises a display 706. The display 706 may be implemented with suitable technologies including, but not limited to at least the following: LCD (liquid crystal display), EL (electroluminescence), LED (light emitting diode), and OLED (organic light emitting diode).

Figure 8:
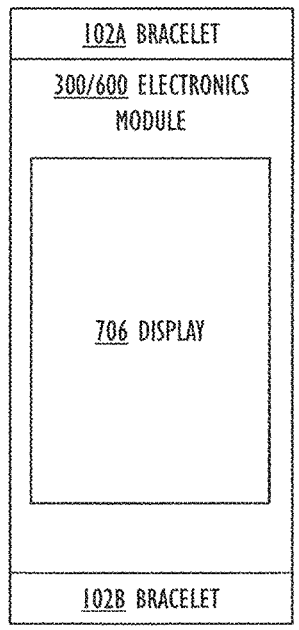

FIG. 8 illustrates an example embodiment of the apparatus 100: a wrist-worn physical activity measurement apparatus with the electronics module 300/600, the display 706 facing outwards, and the bracelet 102A, 1028 for attaching the apparatus 100 to the wrist.

Figure 9:
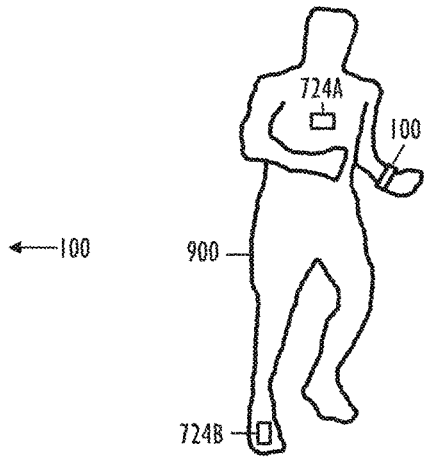

FIG. 9 illustrates an example embodiment of the apparatus 100. The user 900 is provided with the wrist-worn apparatus 100. Furthermore, the user 900 may be provided with a heart rate transmitter 724A strapped around the chest, and possibly also with a shoe-mounted stride sensor 724B. The accessories 724A, 724B communicate wirelessly with the apparatus 100. Various accessories may be flexibly used as needed, i.e. all of them are not necessarily needed all the time, or by all users, or in all use cases.

Next, with reference to FIGS. 10, 11, 12, 13 and 14, let us study example embodiments relating to the use of the apparatus 100.

The apparatus 100 is attached to the left hand (or, naturally, to the right hand) 1000 of the user. The hand 1000 comprise an ulna side 1100 of the wrist, a back of the hand side 1102 of the wrist, a radius side 1104 of the wrist, and a palm side 1106 of the wrist.

FIG. 12 illustrates a cross-section 1108 of the hand 1000, with cross-sections of an ulna bone 1200 and a radius bone 1202.

FIG. 13 illustrates the apparatus 100 being positioned over the wrist 1108. Each link 104 is formed at one side to comprise a part and at the opposite side a counterpart interlocking with a part of an adjacent link 104. The apparatus 100 is attachable around a curvature of the wrist 1108 of the user such that the links 104 and the adjacent links 104 are pivotably lockable in relation to each other in order to wrap and lock around the wrist 1108.

In an example embodiment, the bracelet 102 is dimensioned and adapted such that it is attachable around the wrist 1108 by pressing 1300, 1302, 1304, 1306, 1308, 1310, 1312 in from the outwards towards the wrist 1108 by the user. FIG. 13 is the starting position, wherein the apparatus 100 is positioned over the wrist 1108, whereas FIG. 14 is the finishing position, wherein the apparatus 100 is wrapped and locked around the wrist 1108.

In an example embodiment, also illustrated with FIGS. 13 and 14, the apparatus 100 forms an open loop when in open position such that it is positionable around the wrist 1108 as in FIG. 13, and the apparatus 100 forms an open loop when in closed position wrapped and locked around the wrist 1108 as in FIG. 14, wherein the ends 200, 202 of the bracelet 102 opposite to each other are closer to each other in the closed position of FIG. 14 than in the open position of FIG. 13. In order to take off the apparatus 100, the ends 200, 202 are pulled outwards, whereby the loop opens wider releasing the locking around the wrist 1108.

In an example embodiment, the bracelet 102 does not require a traditional pin buckle or other means of attaching the ends 200, 202 with each other. This is because, as shown in FIG. 14, the open loop wraps and locks around the wrist 1108, and the ends 200, 202 remain free. This solution further enhances the usability of the apparatus 100: attachment is simplified, wearing comfort is increased, and taking off is simplified.

In an example embodiment, the links 104 and the adjacent links 104 are pivotable such that they exert a clamping force 1400, 1402, 1404, 1406 against the wrist 1108.

In an example embodiment a part of the links 104 and the adjacent links 104 are positioned, dimensioned and adapted such that a greater clamping force 1402, 1404 is directed towards ulna and radius bones 1200, 1202 of the wrist 1108 than towards the palm side 1106 of the wrist 1108 and the back of the hand side 1102 of the wrist 1108. This may enhance the wearing comfort of the apparatus 100 even further.

Note that in FIGS. 13 and 14 the flexible casing 106 is not illustrated so clearly as in FIGS. 1, 3, 4, 5 and 6 in order to make the illustration clearer, i.e., the casing 106 is more closely integrated with the links 104.

In an example embodiment, the flexible casing 106 in the inside of the bracelet 102, which comes into contact with the wrist 1108 when attached, comprises non-skid material, such as polyurethane, thermoplastic polyurethane (TPU), silicon, rubber, synthetic rubber, or other material with causes increased friction between the skin of wrist 1108 and the inside of the bracelet 102. Furthermore, said surface of the casing 106 may comprise appropriate texture to increase the friction. The increased friction may aid in preventing the bracelet 102 from moving around the wrist 1108.

Next, with reference to FIGS. 15, 16, 17, 18A, 18B, 19A and 19B let us study further example embodiments of the structure of the apparatus 100, especially relating to the structure and functionality of the links 104.

In an example embodiment, the links 104 are made of suitably rigid material such as plastic, composite or metal. In an example embodiment, the flexible casing 106 is made of plastic, polyurethane, thermoplastic polyurethane (TPU), silicon, rubber, synthetic rubber, or other suitably flexible material. The links 104 form the "backbone" of the bracelet 102, whereas the flexible casing 106, while encasing the links 104, improves the wearing comfort as hair or skin cannot stick between the links 104, and, furthermore, dirt cannot accumulate in spaces between the links 104.

Figure 16:
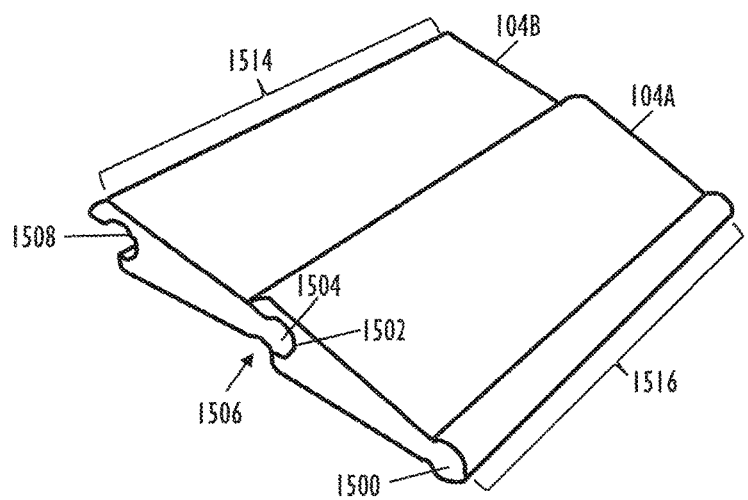

In an example embodiment, illustrated in FIG. 16, the side and the opposite side are two lateral surfaces of the link 104: for the sake of the clarity, the lateral surfaces 1514, 1516 are illustrated from the link 104A and the adjacent link 104B, and the part 1504 and the counterpart 1502 interlock with each other. Alternatively, the side and the opposite side may be defined as two edges (=narrow surfaces) of the link 104. Naturally, these lateral surfaces 1514, 1516 (or edges) need not be straight, i.e., they may comprise also other forms, but in such a way that the link 104A and the adjacent link 104B may be mechanically coupled with each other by the part 1504 and the counterpart 1502 pivotably lockable.

Figure 15:
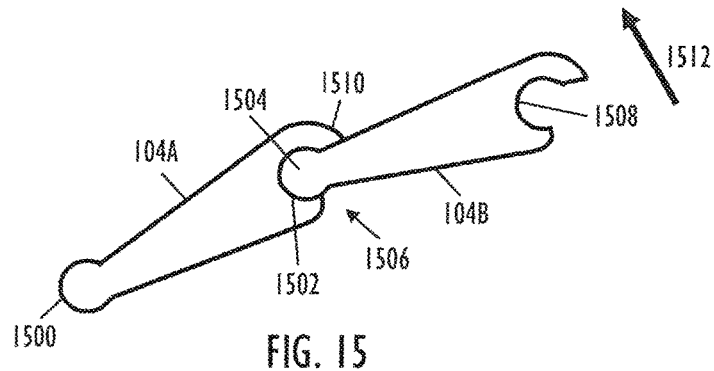
FIGS. 15, 16, 17, 18A, 18B, 19A and 19B illustrate further example embodiments of the structure of the apparatus.

In an example embodiment of FIGS. 15 and 16, the link 104A and the adjacent link 104B are identical. This simplifies the structure of the apparatus 100. However, in an example embodiment, some of the links 104 are identical with each other, whereas some of the links 104 may have a different structure, in order to accommodate the electronics module 300, 600, 602, 604, 606, 608, 610, 612, or in order to fit the curvature of the wrist 1108 better, for example.

In an example embodiment of FIGS. 15 and 16, the part and the counterpart comprise a snap-fit joint 1506. In a snap-fit joint 1506, the part and the counterpart comprise locating and locking features. The locking features move aside for engagement with a mating part, followed by a return of the locking feature toward its original position. The locating features are inflexible, providing strength and stability.

In an example embodiment of FIGS. 15 and 16, the part and the counterpart comprise a ball 1504 and a socket 1502 joint 1506. In an example embodiment, the socket 1502 forms the locking features, whereas the ball 1504 forms the locating features of the snap-fit joint. As can be seen in FIGS. 15 and 16, the links 104A, 104B are identical, comprising further a ball 1500 and a socket 1508 to mate with their adjacent links 104.

Figure 17:
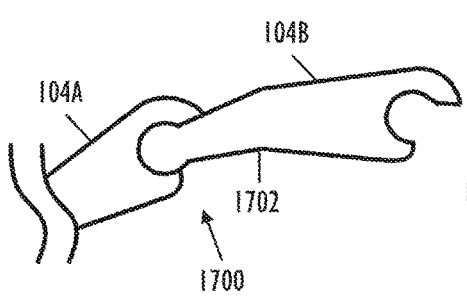

In an example embodiment of FIG. 17, the part and the counterpart comprise an eccentric joint 1700. In an example embodiment, the eccentric joint 1700 comprises a bending 1702 in the link 104B such that the link 104B more naturally follows the curvature of the wrist 1108.

Figures 18A, 18B:
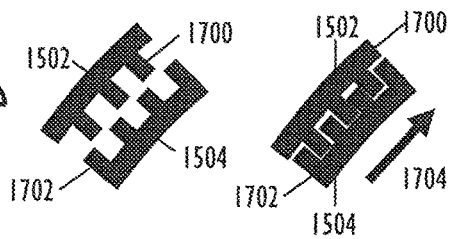

In an example embodiment, the part and the counterpart comprise a gear wheel mechanism causing that the links 104A and the adjacent 104B links are pivotable in relation to each other stepwise. In an example embodiment of FIG. 18A, the ball 1504 comprises cogs 1702 and the socket 1502 comprises matching cogs 1700. FIG. 18B shows the gear wheel mechanism in action: as the ball 1504 rotates into direction 1704, the cogs 1702 of the ball 1504 move in relation to the cogs 1700 of the socket 1502 stepwise, locking into each position. In order this to work, the cogs 1700 and/or the cogs 1702 are made of flexible material such as plastic.

In an example embodiment, the apparatus 100 further comprises friction structures causing friction between the part and the counterpart as the link 104A and the adjacent link 104B are moved relative to each other. The purpose of such friction is to achieve a predetermined stiffness to the joint between the link 104A and the adjacent link 104B so that they are pivotably lockable in relation to each other in order to wrap and lock around the wrist 1108. Such friction structures may employ suitable dimensioning, and/or suitable texturing, and/or suitable geometry of the part and the counterpart.

In an example embodiment, the apparatus 100 further comprises feedback structures causing senseable feedback to the user while pivoting the links 104 and the adjacent links 104. In an example embodiment, the cogs 1700, 1702 generate the feedback, which the user may sense (by feeling and/or hearing, for example). In another example embodiment, the friction structures generate the feedback.

Figure 19A:
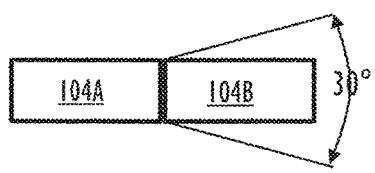
Figure 19B:

In an example embodiment of FIGS. 19A and 19B, the part and the counterpart are positioned, dimensioned and adapted such that the links 104A and the adjacent links 104B are pivotable in relation to each by a limited angle. In an example embodiment, the limited angle is 30 degrees or less. In an example embodiment, the limited angle is 15 degrees or less. In an example embodiment, the limited angle is 9 and 15 degrees. In an example embodiment, the part and the counterpart are positioned, dimensioned and adapted such that the link 104A and the adjacent link 104B may, from the initial position, only pivot towards the wrist 1108. This is shown in FIG. 15, wherein the structure 1510 prohibits the turning of the adjacent link 104B into a direction 1512.

It will be obvious to a person skilled in the art that, as technology advances, the inventive concept can be implemented in various ways. The invention and its embodiments are not limited to the example embodiments described above but may vary within the scope of the claims.

The invention claimed is:

1. A wrist-worn physical activity measurement apparatus comprising:
   an inelastic bracelet comprising a first end, a second end and a plurality of links therebetween, each link being formed at one side to comprise a part and at an opposite side a counterpart interlocking with the part of an adjacent link, except for the links that form the first and second ends, which are only interlocked on one side;
   a flexible casing surrounding the plurality of links, wherein the apparatus is attachable around a curvature of a wrist of a user such that the links and the adjacent links are pivotably lockable in relation to each other in an open position and a closed position in order to wrap and lock around the wrist while the first and second ends of the bracelet remain unconnected in the closed position, wherein the apparatus forms an open loop when in the open position such that it is positionable around the wrist, and the apparatus forms an open loop when in the closed position wrapped and locked around the wrist, wherein the first and second ends of the bracelet are closer to each other in the closed position than in the open position, but are not connected to each other; and
   an electronics module coupled with the bracelet, wherein the part and the counterpart are positioned, dimensioned and adapted such that the links and the adjacent links are pivotable in relation to each by a limited angle.

2. The apparatus of claim 1, wherein the electronics module is attached to at least one of the links.

3. The apparatus of claim 1, wherein the electronics module is attached between two of the links.

4. The apparatus of claim 1, wherein at least one of the links is a special link, in which the electronics module is integrated.

5. The apparatus of claim 1, wherein the electronics module comprises at least one of a biosignal measurement sensor, a processor module comprising one or more processors and one or more memories including computer program code.

6. The apparatus of claim 1, wherein the electronics module comprises: a sensor for measuring physical activity of the user, an electronic circuit for wireless communication, one or more processors, and one or more memories including computer program code.

7. The apparatus of claim 1, wherein the bracelet is dimensioned and adapted such that it is attachable around the wrist by pressing it from outwards towards the wrist by the user.

8. The apparatus of claim 1, wherein the links and the adjacent links are pivotable such that they exert a clamping force against the wrist.

9. The apparatus of claim 8, wherein the links and the adjacent links are positioned, dimensioned and adapted such that a greater clamping force is directed towards ulna and radius bones of the wrist than towards the palm side of the wrist and the back of the hand side of the wrist.

10. The apparatus of claim 1, wherein the flexible casing in the inside of the bracelet, which comes into contact with the wrist when attached, comprises non-skid material.

11. The apparatus of claim 1, wherein the link and the adjacent link are identical.

12. The apparatus of claim 1, wherein the part and the counterpart comprise a snap-fit joint.

13. The apparatus of claim 1, wherein the part and the counterpart comprise a ball and a socket joint.

14. The apparatus of claim 1, wherein the part and the counterpart comprise an eccentric joint.

15. The apparatus of claim 1, wherein the part and the counterpart comprise a gear wheel mechanism causing the links and the adjacent links to be stepwise pivotable in relation to each other.

16. The apparatus of claim 1, further comprising friction structures causing friction between the part and the counterpart as the link and the adjacent link are moved relative to each other.

17. The apparatus of claim 1, further comprising feedback structures causing senseable feedback to the user while pivoting the links and the adjacent links.

* * * * *